US006393404B2

(12) United States Patent
Waters et al.

(10) Patent No.: US 6,393,404 B2
(45) Date of Patent: *May 21, 2002

(54) SYSTEM AND METHOD FOR OPTIMIZING MEDICAL DIAGNOSIS, PROCEDURES AND CLAIMS USING A STRUCTURED SEARCH SPACE

(75) Inventors: A. Bryan Waters, Rowlett; Gerald J. C. Rae, Coppell, both of TX (US)

(73) Assignee: Ker Bugale, Inc., Pebble Beach, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/219,048

(22) Filed: Dec. 23, 1998

(51) Int. Cl.[7] .............................................. G06F 17/60
(52) U.S. Cl. ............................................. 705/2; 705/4
(58) Field of Search .................................. 705/2, 3, 4

(56) References Cited

U.S. PATENT DOCUMENTS

| | | | | |
|---|---|---|---|---|
| 3,839,708 A | * | 10/1974 | Bredesen et al. | ........... 395/112 |
| 4,315,309 A | * | 2/1982 | Coli | |
| 4,408,181 A | * | 10/1983 | Nakayama | ................. 382/306 |
| 4,491,725 A | | 1/1985 | Pritchard | |
| 4,553,206 A | * | 11/1985 | Smutek et al. | .............. 707/101 |
| 4,667,292 A | | 5/1987 | Mohlenbrock et al. | |
| 5,001,630 A | | 3/1991 | Wiltfong | |
| 5,018,067 A | | 5/1991 | Mohlenbrock et al. | |
| 5,077,666 A | | 12/1991 | Brimm et al. | |
| 5,253,164 A | | 10/1993 | Holloway et al. | |
| 5,301,105 A | | 4/1994 | Cummings, Jr. | |
| 5,325,293 A | | 6/1994 | Dorne | |
| 5,557,514 A | | 9/1996 | Seare et al. | |
| 5,583,758 A | | 12/1996 | McIlroy et al. | |
| 5,835,897 A | | 11/1998 | Dang | |
| 5,845,253 A | | 12/1998 | Rensimer et al. | |
| 5,845,254 A | | 12/1998 | Lockwood et al. | |
| 5,915,241 A | | 6/1999 | Ginnini | |

FOREIGN PATENT DOCUMENTS

JP    11161704 A   *   6/1999

OTHER PUBLICATIONS

Gear, W., 'Applications and Algorithms in Science and Engineering', 1978, Science Research Associates, Inc., Intro to Computers: Structured Programming, and Applications, Module A. Chap A12.*

Gilbert, Jennifer A., "Physician Data Entry: Providing Options is Essential," Health Data Management, Sep. 1998, pp. 84–92.

"Smaller View is Coming for the Expanding Web," New York Times, Thursday, Oct. 1, 1998.

(List continued on next page.)

Primary Examiner—Sam Rimell
(74) Attorney, Agent, or Firm—Winstead Sechrest & Minick P.C.

(57) ABSTRACT

A system and method for optimizing medical diagnosis, procedures and reimbursement claims using a structured search space is described. The system may comprise: a master procedure list of alphanumeric codes that represent each of a plurality of medical procedures, wherein the master procedure list includes simple procedures and compound procedures which consist of at least two simple procedures; a value associated with each of the plurality of medical procedures; a list of ordered procedures listing medical procedures for a specific medical encounter; a search tree of all possible combinations of the simple procedures and the compound procedures in the list of ordered procedures; and a minimum total of the values associated with the medical procedures in the list of ordered procedures.

28 Claims, 4 Drawing Sheets

OTHER PUBLICATIONS

Austen, Ian, "Unleashing the Power of the Pen," New York Times, Thursday, Oct. 1, 1998.

Gotcher, Renee, "Space–age Health Care," www.infoworld.com, Infoworld, Oct. 5, 1998.

New Computer Software That Will Help Identify and Correct Coding Errors on Bills for Multiple Surgical Procedures is Being Used by the Employee Benefits Division of Aetna Life & Casualty, News Release, Feb. 26, 1990, paragraph 5.

O'Connor, K., Electronic Claims: Still Buyer Beware? Business and Health, Sep. 1991, vol. 9, No. 9, pp. 52–58.

Goody, B. et al., New Directions for Medicare Payment Systems. Health Care Financing Review, Winter 1994, vol. 16, No. 2, pp. 1–12.

Baum, D. Health Care Industry Uses Expert Systems Technology Data Based Advisor, Jul. 1995. vol. 13, No. 6, pp. 38–40.

Whetshell, G. W. The History and Evolution of Hospital Payment Systems. Nursing Administration Quarterly. Summer 1999. vol. 23, No. 4.

* cited by examiner

SYSTEM AND METHOD FOR OPTIMIZING MEDICAL DIAGNOSIS, PROCEDURES AND CLAIMS USING A STRUCTURED SEARCH SPACE

FIELD OF THE INVENTION

The present invention relates generally to a system and method to optimize medical diagnosis, procedures and reimbursement claims using a structured search space.

BACKGROUND FOR INVENTION

The Health Care Finance Administration, hereinafter referred to as HCFA, is a government agency responsible for the operation of oversight of medical insurance programs such as Medicare and Medicaid. These programs handle medical claims submitted by health care providers, such as doctors, hospitals, and skilled nursing facilities and reimburse claims that are valid. In recent years, to stop intentional and unintentional overbilling, Medicare has implemented fraud control and medical necessity initiatives that place an enormous burden upon health care providers to avoid unintentional mis-billings.

Medicare billing is based on two sets of codes: the diagnosis code and the procedure code. The diagnosis code represents the diagnosed illness or malady or in some cases just the fact that the patient is having a routine checkup. The procedure code represents the procedure being ordered and is associated with the diagnosis code on the basis of medical necessity. In other words, each diagnosis code has a set of related procedures that can be ordered and will, barring any other mitigating circumstances, be reimbursed by Medicare. Procedure codes are reimbursed based upon a set fee schedule determined and set by HCFA. Procedure codes can represent a simple procedure or a compound procedure that represents multiple individual procedures. This allows for more than one procedure code sequence to represent the exact same set of procedures performed. One consequence of this is that one code combination will allow for a larger reimbursement than another code sequence for the same services performed.

As a result of the recent health care reform mentioned earlier, HCFA has specified that when determining proper coding for procedures any logic that groups payable procedures in a manner which yields the least expensive payment is acceptable. As a rule, duplicate procedures are not reimbursable. That is, the same health care provider cannot get reimbursed for performing the same procedure on the same patient more than once for a given encounter. Exceptions to this rule can be indicated in the reimbursement claim by adding a modifier code to the main procedure code which effectively makes it a completely new code.

There are two types of procedure codes that can be used by a health care provider to specify the procedures ordered. The first type are CPT (Common Procedural Terminology) codes that were developed by the American Medical Association (AMA). The second type are HCPCS (Health Care Procedural Coding System) codes that were developed by HCFA to address issues with the CPT codes as they relate to medical billing.

Therefore, what is needed is a system and method to assist in providing the health care professional assistance in selecting medical procedures for a given medical diagnosis. In addition, an optimization of the medical procedures prescribed for a particular medical encounter is also needed. Given the complexity of all of the possible medical procedures, a system and method that provides a medical professional with the least cost combination of the medical procedures ordered is also needed. In addition, the system has to follow the coding practices prescribed by Medicare.

SUMMARY OF THE INVENTION

The present invention addresses all the needs mentioned above. The present invention is a system and method that takes a given set of ordered medical procedure codes and constructs a search space representing all possible combinations of simple and compound procedures, which is then traversed in a systematic manner using an evaluation method for each node that determines the reimbursable value. The traversal continues through the entire search space until a node or graph is located that represents a procedure code combination reflecting the minimum reimbursement possible. The rest of the search space is then traversed and new combinations are compared to the current minimum combination. If a lower combination is found, the current minimum combination is then replaced. This process continues until the entire search space is traversed resulting in the lowest reimbursement combination that satisfies the set of the original ordered procedures.

The system and method can be implemented in a general purpose computer or a portable computer. One embodiment is implemented on a palm sized computer with the medical professional entering medical diagnosis and selecting medical procedures directly. The system would then optimize the ordered procedures for billing and patient encounter recording purposes.

In another embodiment, the attending medical professional records the medical diagnosis and ordered medical procedures and then another medical professional enters the information into a general purpose computer.

The system also has access or a direct connection to the patient's information and/or medical history. The invention would be part of an all purpose medical diagnosis/procedure/billing system, or a standalone software package that finds the optimized billing for Medicare reimbursement from a listing of ordered medical procedures.

In addition, a system and method for optimizing medical diagnosis, procedures and reimbursement claims using a structured search space is described. The system may include: a master procedure list of alphanumeric codes that represent each of a plurality of medical procedures, wherein the master procedure list includes simple procedures and compound procedures which consist of at least two simple procedures; a value associated with each of the plurality of medical procedures; a list of ordered procedures listing medical procedures for a specific medical encounter; a search tree of all possible combinations of the simple procedures and the compound procedures in the list of ordered procedures; and a minimum total of the values associated with the medical procedures in the list of ordered procedures.

BRIEF DESCRIPTION OF DRAWINGS

A better understanding of the present invention can be obtained when the following detailed description of the preferred embodiment is considered in conjunction with the following drawings, in which.

DETAILED DESCRIPTION

Figure 1:
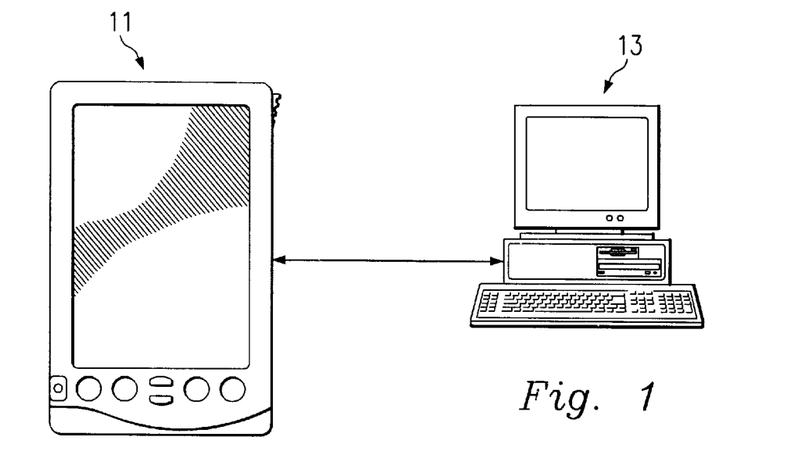
FIG. 1 shows a screen of the preferred embodiment implemented on a palm sized computer.

The preferred embodiment is implemented on a palm sized computer 11 as depicted in FIG. 1, but could also be implemented on a desktop general purpose computer. First, patient information, diagnosis codes and procedures codes would be input into the general purpose computer 13 through direct input or some other type of communication. The diagnosis codes and procedure codes would be obtained from the AMA and the HCFA. In addition, the diagnosis codes and procedures codes would be updated as the HCFA and AMA make changes to their codes. Once this information is in the general purpose computer 13, it would be downloaded onto the palm sized computer. However, all of the information could be directly inputted into the palm sized computer if desired.

In addition, although the preferred embodiment has a medical professional operating a palm sized computer, the invention could also be implemented on a desktop computer and be operated on by a billing clerk, laboratory personnel, or other medical personnel. For example, the billing clerk would use it to validate the billed claim was correct. Moreover, the laboratory personnel would use it to determine if tests have been ordered that will not be reclaimable. These are just two examples of a multitude of uses of the present invention.

Moreover, the preferred embodiment has all the diagnosis and procedure codes already provided in the implementation. Furthermore, the user will configure the system to select only the codes that the medical practice requires on a daily basis. However, the patient information would either be entered directly into the system or the system would be connected electronically to the patients records to also allow the medical professionals patient schedule and the patient treatment history to be loaded into the system.

Operation of the Preferred Embodiment

Figure 2:
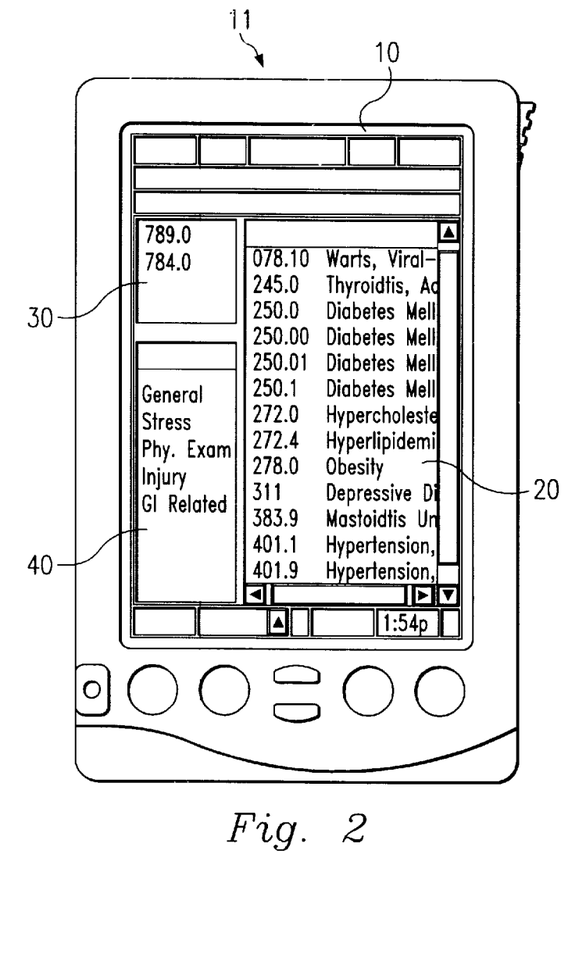
FIG. 2 shows another screen of the preferred embodiment implemented on a palm sized computer.

The preferred embodiment of the invention is implemented on a palm sized computer with the medical professional selecting medical diagnosis and selecting medical procedures directly. FIG. 2 shows an example of a screen 10 of a palm-sized computer 11 that is used to implement the invention. The medical professional would first locate the patient data and then diagnose the medical situation. One window 40 shows a list of diagnosis code groups in order to reduce the number of diagnosis codes from which to chose. Another window 20 shows detail of all of the diagnosis codes that are associated with the selected code group. As the medical professional diagnoses the patient's condition, another window 30 shows the selected diagnosis codes.

Figure 3:
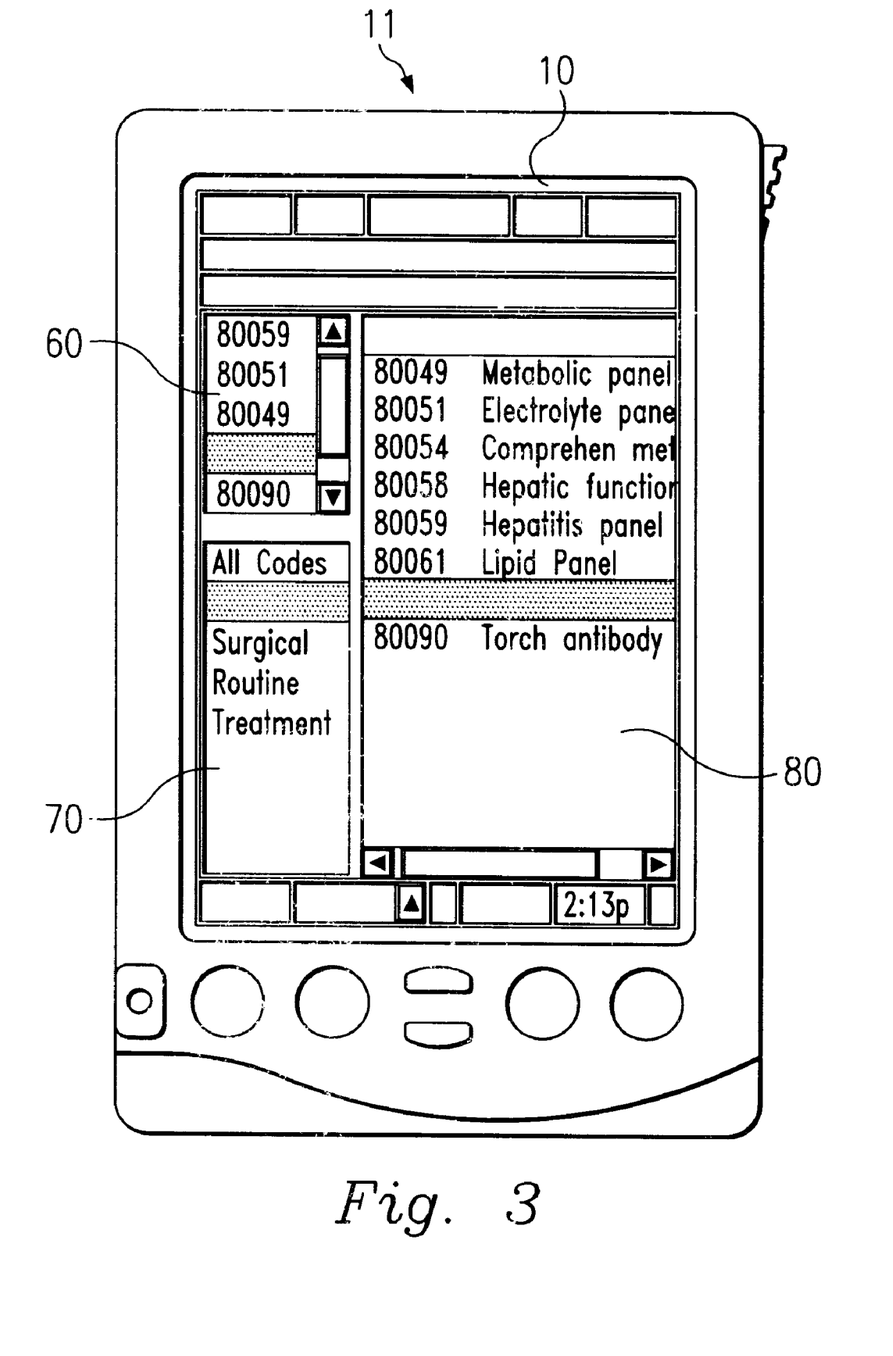
FIG. 3 shows a diagram that represents a list of alphanumeric codes that represent medical procedures prior to being processed by Phase I of the preferred embodiment.

FIG. 3 shows a screen after the medical professional has finished his diagnosis and is now ready to order medical procedures to address the patient's condition. The medical professional would select the medical procedure group to start from in order to select the ordered procedures. One window 70 shows the ordered procedures groups, while another window 80 shows the codes and details of the medical procedures in the selected group. As the medical professional selects the procedures to perform on the patient, those ordered procedures are shown in another window 60. After the medical professional is finished listing the ordered procedures, the system can optimize the ordered procedures for billing.

Another embodiment has the attending medical professional record the medical diagnosis and ordered medical procedures and then another medical professional would enter the information into a general purpose computer.

The system also has access or a direct connection to the patient's information and/or medical history. The invention would be part of an all purpose medical diagnosis/procedure/billing system, or a standalone software package that finds the optimized billing for Medicare reimbursement from a listing of ordered medical procedures.

The Software Optimization System and Method

The following data structures and data are defined for the purpose of this description.

Ordered Procedures

A set of non-optimized codes as the data to be operated on and transformed by the process hereafter known as the ordered procedures. The ordered procedures are used as input to the process.

TABLE 1

| Codes |
|---|
| 1008 |
| C001 |

Table 1 shows an example of two procedure codes, 1008 and C001. 1008 is a simple procedure and C001 is a compound procedure. Procedures can be simple procedures or compound procedures that consist of more than one simple procedure (compound procedures will be interchangeably used with panels throughout this description).

Master Procedure List

The master procedure list is made up of reference data records and will be explained with reference to table 2 below.

TABLE 2

| Codes | Short Description | Long Description | Reimb. Fees |
|---|---|---|---|
| 1004 | short desc. 1 | long desc. 1 | $2.00 |
| 1005 | short desc. 2 | long desc. 2 | $1.00 |
| 1006 | short desc. 3 | long desc. 3 | $4.00 |
| 1008 | short desc. 4 | long desc. 4 | $5.00 |
| C001 | short desc. 5 | long desc. 5 (1004, 1005) | $3.00 |
| C002 | short desc. 6 | long desc. 6 (1004, 1006) | $4.00 |
| C003 | short desc. 7 | long desc. 7 (1005, 1008) | $5.50 |

The master procedure list has a reference data record for all possible procedures with their associated identification codes. Each reference data record also includes a short description, a long description, and associated reimbursement fees. The long description also contains a listing of all of the simple procedures if that record is for a compound procedure. The master procedure list and its required data structures are used during the process to provide the fees, and the components of compound procedures, for determining new possible combinations.

Output Data

A set of procedure codes that are derived from the ordered procedures by using different combinations of the compound and simple procedure codes that represent the minimal reimbursement possible. This output data is hereafter referred to as billable procedures.

The process is first presented with a list of procedure codes to be optimized. This list of procedures can contain duplicates (the same procedure ordered more than once) and any combination of simple procedures and/or panels.

The optimization process will be described in three phases. Phase I is the preparation phase whereby the input data is processed to remove compound procedures or duplicate procedures. Phase II is the construction of the search space. Phase III is the traversal of the search space to locate the optimum billing structure.

Phase I—Preparation of Input Data

The ordered procedures are checked to see if any of the procedures are panels by comparing each ordered procedure with the master procedure list and then checked for duplicate procedures. It is important to note that the duplicates check is to determine whether a simple procedure is ordered more than once which requires that any compound procedures or panels be unbundled (disassembled) prior to removal of duplicates.

For each entry in the ordered procedures list a search is performed to determine whether the entry is a panel as indicated by the presence of a list of component procedures in the master procedure list for the ordered procedure code in question. If an ordered procedure is determined to be a panel then the procedure code is removed from the ordered procedure list and the components of the panel are added to the ordered procedure list. This process is performed recursively for each procedure in the ordered procedures list until all procedures in the ordered procedures list are simple (non-panel) procedures. The unbundling process will require either a recursive implementation or a multi-pass implementation if a panel or compound procedure exists that has another compound procedure as a component.

After unbundling all compound procedures the list is processed again to remove any duplicate procedure codes. Beginning with the first entry in the list each entry is compared to all remaining entries in the list looking for duplicates. When a duplicate is found, it is removed from the list and the process continues until no more duplicates remain.

Phase II—Construction of the Search Space

The construction of the search space requires inputting the set of ordered procedures with all compound procedures unbundled and all duplicate procedures removed, as described in Phase I. The search space construction involves building a set of data structures that represent all possible combinations of compound and simple procedures. For example, a set of simple procedure codes would be billable as Panel 42 (note: these panel names do not represent real panels as used by HCFA and are for the purpose of illustration only) and Panel 28 with a few simple procedures remaining. Alternately, they would be billable as Panel 38 with no other Panels or simple procedures. Finally, they would be billable as a collection of simple procedure codes using no panels. The search space must represent all possible combinations of codes using compound procedures and simple procedures.

After unbundling the compound procedures and removing the duplicates, the ordered procedures list is then used to start a methodical combination of the processed procedure list into various compound/simple procedure combinations.

Prior to processing, a list of all compound procedures is made. Then, the first step of the recursive process is to examine the ordered procedure list to find a match between the components of the compound procedures and the ordered procedures. A matched compound procedure is produced when the components of that procedure match two or more of the ordered procedures. The component procedures of this newly matched compound procedure are then removed from the ordered procedures. The matched compound procedure code is then added to the ordered procedure list. The matched compound procedure is then removed from the selection list and the process is repeated until all compound procedures have been either used or discarded as a non-match. For each combination that has been started in this manner, the remaining simple procedures are now searched again to determine if there are any more compound procedure combinations that can be made. If so, the component procedures are then removed, the compound procedure code added and the remaining procedures are again searched until no more compound matches are found. This process is repeated until all combinations of compound procedures and simple procedures are found. The pseudocode below and the software code in Appendix A further illustrate how the search space can be constructed.

In addition, the following example illustrates construction of this search space.

Master Reference List (also Depicted in Table 2)
1004
1005
1006
1008
C001 (PANEL including 1004, 1005)
C002 (PANEL including 1004, 1006)
C003 (PANEL including 1005, 1008)
Ordered Procedures (before Phase I—also Depicted in Table 1)
C001 and 1008
Ordered Procedures (after Phase I)
1004, 1005, 1008
Phase II (Depicted in FIG. 6)
1.0—1004, 1005, 1008 (shown as node 82)
2.0—C001* (node 84)
   2.1—1008 (node 86)
   2.2—C003 (node 88)
3.0—C002* (node 90)
   3.1—1005, 1008 (node 92)
   3.2—C001* (node 94)
      3.2.1—1008 (node 96)
      3.2.2—C003 (node 98)
   3.3—C003* (node 100)
      3.3.1—1005 (node 102)
      3.3.2—C001 (node 104)
4.0—C003* (node 106)
   4.1—1004 (node 108)
   4.2—C001 (node 110)

The branches of the outline marked with asterisks are incomplete and have sub-branches that are needed to complete that combination chain by selecting one of the sub-components of that branch of the outline. For example, entry 1.0 is complete and corresponds to the input list. Branch 2.0 starts with the compound procedure C001 and can be completed by selecting either 2.1 or 2.2 making either [C001, 1008] or [C001, C003] a complete combination.

The following list represents all possible combinations using these codes:
[1004, 1005, 1008]
[C001, 1008]
[C001, C003]
[C002, 1005, 1008]
[C002, C001, 1008]
[C002, C001, C003]
[C002, C003, 1005]
[C002, C003, C001]
[C003, 1004]
[C003, C001]

Phase III—Traversal of the Search Space Using Desired Optimization Criteria

The traversal phase requires a set criteria for evaluating the combination that is most appropriate for being identified in the search space. The primary criteria that is being used for this embodiment is minimum reimbursement with secondary emphasis placed on the least number of procedure codes in the combination. In the case where two procedure combinations have different reimbursement rates, the procedure with the lesser of the two rates will be selected. In the case where the reimbursement rates are the same, either the combination using the least number of procedure codes or the combination of the maximum compound procedure codes with the minimum simple procedure codes would be selected.

Performing this traversal requires setting a global minimum fee indicating the lowest total in fees for a procedure combination. While traversing the search space, the fees for each combination are summed to obtain the total fee for that combination. This fee is then compared with the current global minimum fee. If the current fee is less than the global minimum, then the global minimum is set to the current fee and the current combination is saved as the current minimum combination. Each combination is processed exhaustively in this manner until all combinations have been reviewed. The summing process requires the fee for each component of the combination to be found and added to the running total, thus building the total fee for combination. During the fee building process the running total is described to be the partial fee. When all components of the combination have been found and added the partial fee becomes the total fee for the combination. The process can be optimized to reject combinations by calculating and comparing the partial fee with the current global minimum. If the partial fee exceeds the current global minimum, then the entire combination is rejected. This eliminates the need for further checking of the search space below the partial combination and thereby reduces any unnecessary review of combinations that would exceed the global minimum.

Figure 4:
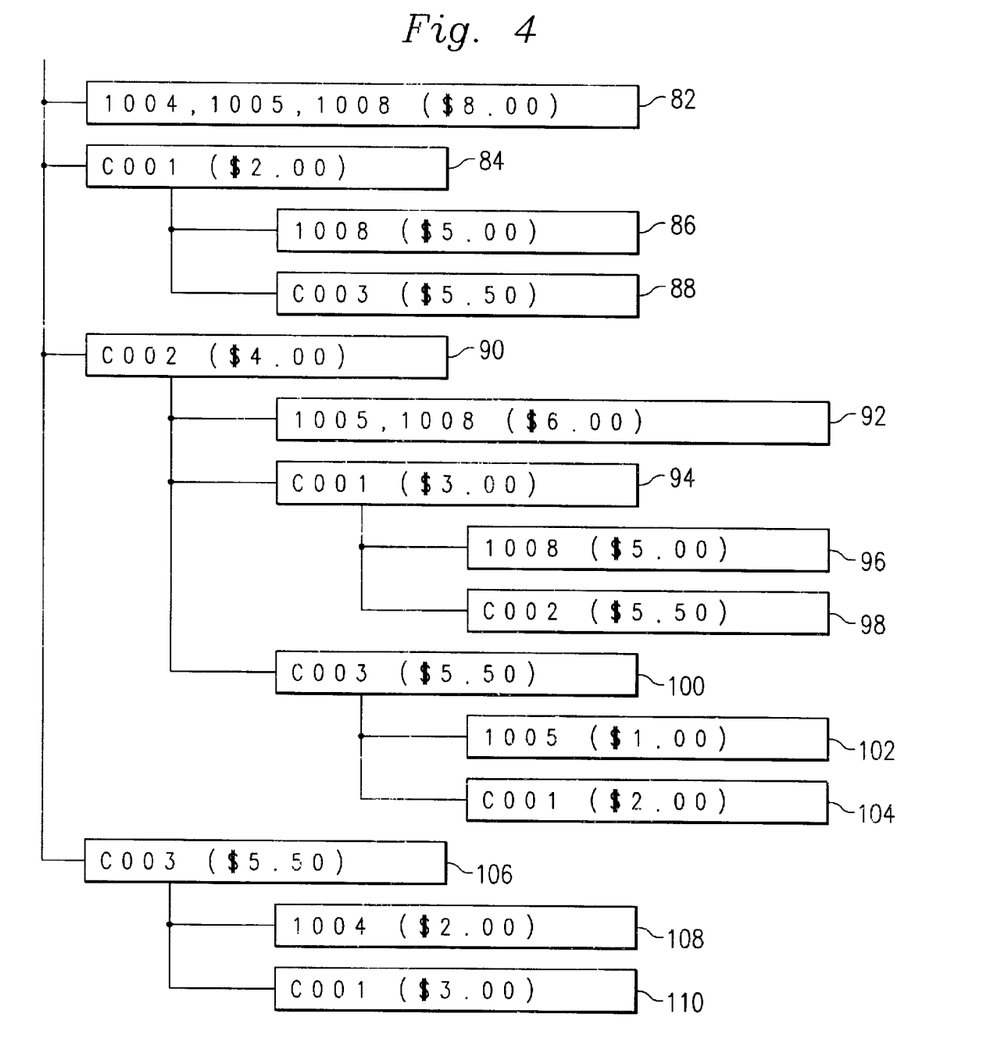
FIGS. 4–5 show diagrams that represent a tree-like search space that was constructed using the alphanumeric codes shown in FIG. 3 and using the reference list shown in FIG. 2 that was created by Phase II of the preferred embodiment.
Figure 5:
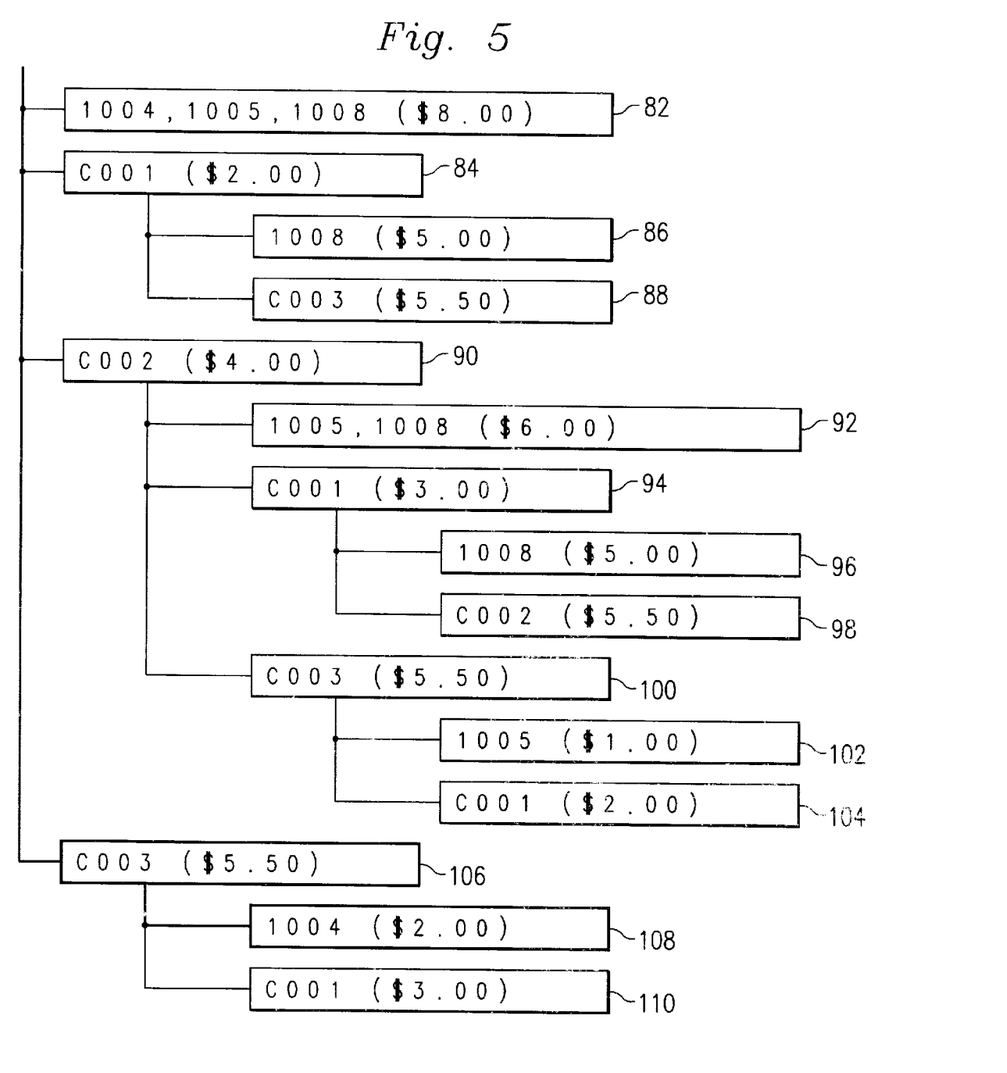

FIG. 5 shows the search tree depicted in FIG. 4 with the minimum branch outlined as the combination of compound procedure C003 (node 106) and simple procedure 1004 (node 108). This combination includes all of the original procedures in the procedure list (1008 and C001—shown in FIG. 3) and has the minimum total cost ($7.50) for all of the procedures in the original procedure list.

An Example of Pseudocode for Preferred Embodiment

A pre-built incremental search tree is now described for illustration purposes. This implementation does not include search optimization techniques in order to clarify the technique. This example also uses the tree structure illustrated in FIG. 3 to create a search tree.

GetChildCount(NODE)—returns number of children or 0 if none exists.

InsertChildNode(NODE, CHILD NODE)—inserts a reference to CHILD NODE into NODE

Count(LIST)—returns number of entries in list

NewNode(LIST)—creates a new NODE and associates the LIST with the NODE. Note that the list and the CHILD NODES are not the same thing. The LIST parameter is stored with value semantics with the NODE while the CHILD NODES are completely separate NODES that have their own values stored in the form of LISTs.

Procedures(PANEL)—Returns a LIST that contains the unbundled procedure codes for the specified panel.

Procedures(NODE)—Same as Procedures (PANEL) except it returns the LIST of procedures that is associated with the NODE.

PanelCode(PANEL)—Returns a LIST that contains 1 entry corresponding to the PANEL code. Note this single entry is returned as a LIST for the purpose of symmetry only. Since each NODE of the search space stores a list of codes, it makes the algorithm cleaner if PANEL codes are stored that way as well.

GetChild(P,I)—Returns a NODE that corresponds to the Ith child NODE to NODE P.

CalcValue(NODE)—Returns a value that corresponds to the sum of the regional Medicare reimbursement values for each procedure in the list returned by calling Procedures (NODE).

Intersection(LIST,LIST)—Returns a LIST that is the intersection of the LIST structures passed for arguments.

Subtraction(LIST1,LIST2)—Returns a LIST that contains all of the elements in LIST1 that are not also in LIST2.

```
HasPartialMatch
FUNCTION UnbundleCodes(ProcList)
    NPROCS = Count(ProcList)
    NPANELS = Count(PanelList)
    PanelProcList = NULLPROCLIST
    FOR I = 1 TO NPROCS
        FOR J = 1 to NPANELS
            If ProcList(I) = PanelCode(PanelList(J)) THEN
                ProcList(I) = Procedures(PanelList(J))
                BREAK
            END IF
        END FOR
    END FOR
    RETURN ProcList
END FUNCTION
ROUTINE BuildSearchTree(P,ProcList)
    Q = NEWNODE(ProcList)
    InsertChildNode(P,Q)
    N = Count(PanelList)
    FOR I = 1 to N
        IF HasPartialMatch(ProcList,PanelList(I)) THEN
            PanelProcList = ProcList & Procedures(PanelList(I))
            Q = NEWNODE(PanelCode(PanelList(I)))
            InsertChildNode(P,Q)
            RemainingProcList = ProcList & (~PanelProcList)
            BuildSearchTree(Q,RemainingProcList)
        END IF
    END FOR
END ROUTINE
FUNCTION GetLocalMinimum(P)
    MinVal = +INFINITY
    N = GetChildCount(P)
    FOR I = 1 to N
        Q = GetChild(P,I)
        IF GetChildCount(Q) >0 THEN
            Val = GetLocalMinimum(Q)
        ELSE
            Val = 0
        Val = Val + CalcValue(Q)
        IF MinVal > Val THEN
            MinVal = Val
    END FOR
    RETURN MinVal
END FUNCTION
```

```
Root = NEWNODE(null)
UnbundledProcList = UnbundleCodes(ProcOrderList)
BuildSearchTree(Root,UnbundledProcList)
Reimbursement = GetLocalMinimum(Root)
```

A more detailed implementation is also included as Appendix A to demonstrate how the preferred embodiment would be implemented in the "C" computing language.

The present invention has been described in connection with the preferred embodiment as described herein. Although an embodiment has been shown and described in detail herein, along with the certain variants thereof, many other varied embodiments that incorporate the teachings of the invention may be easily constructed by those skilled in the art. Accordingly, the present invention is not intended to be limited to specific form set forth herein, but on the contrary, it is intended to cover such alternatives, modifications, and equivalents, as can be reasonably included within the spirit and scope of the invention as defined by the following claims.

APPENDIX A

```
#include <stdio.h>
#include <stdlib.h>
#include <string.h>
#include <stdlib.h>
#include <ctype.h>
#include <assert.h>
#include <bitvector.h>
#include <list.h>
struct Procedure : public Object {
  char *code;
  char *desc;
  double fee;
  int isPanel; //indicates whether procedure is a panel
  BitVector panelProcs; //if is panel, this contains the panel codes
};
struct TreeNode : public Object {
  BitVector procedures; //list of procedures for this branch
  List branches;
};
int numProcedures = 0;
Procedure *procedures = NULL ; // array of procedures
TreeNode rootNode;
int findCode(char *code)
{
  for(int i=0;i<numProcedures;i++)
    if( strcmpi(procedures[i].code,code)==0) return i;
  return -1;
}
void trimString(char *str)
{
  char *p = str;
  while(isspace(*p)) p++;
  int len = strlen(p);
  memcpy(str,p,len);
  str[len] = 0;
  len = strlen(str);
  if( len) {
    p = str+(strlen(str)-1);
    while(p>=str &&isspace(*p)) *p-- = 0;
  }
}
void loadPanelDefinitions(char *filename)
{
  FILE *fp = fopen(filename,"r");
  assert(fp);
  char buf[1024];
  //load the panel definitions
  while(fgets(buf,sizeof(buf),fp)) {
    trimString(buf);
    // get code and procedure
    char *p = strtok(buf,",");
    int id = findCode(p);
    if( id >= 0) {
      Procedure *panel = &procedures[id];
      panel->isPanel = TRUE;
      while(p=strtok(NULL,",")) {
        int pid = findCode(p);
        if( pid >= 0)
          panel- >panelProcs.set(pid);
      }
    }
  }
  fclose(fp);
}
void buildProcedureList(char *filename)
{
  FILE *fp = fopen(filename,"r");
  assert(fp);
  char buf[1024];
  // get the first line containing the number of procedures
  fgets(buf,sizeof(buf),fp);
  numProcedures = atoi(buf);
  assert(numProcedures>0&&numProcedures <20000); // the 20000 cap is arbitrary just for sanity's sake
  // allocate the array of codes
  procedures = new Procedure[numProcedures];
  assert(procedures)
  //load the procedures;
  int i = 0;
  while(fgets(buf,sizeof(buf),fp)) {
    trimString(buf);
    // get code
    char *p = strtok(buf,", ");
    procedures[i].code = strdup(p);
    procedures[i].isPanel = FALSE;
    // get fee
    p = strtok(NULL,",");
    procedures[i].fee = atof(p);
    // get desc
    p = strtok(NULL,"");
    if(p) {
      while(*p&&(isspace(*p)| |*p ==',')) p++;
      procedures[i].desc = strdup(p);
    }else
      procedures[i].desc = strdup ("");
//printf("%s,%f,%s\n",procedures[i].code,procedures[i].fee,procedures[i].desc);
    i++;
  }
  fclose(fp);
}
BitVector *loadOrders(char *filename)
{
  BitVector *orders = new BitVector;
  assert(orders);
  FILE *fp =fopen(filename,"r");
  assert(fp);
  char buf[1024];
  //load the panel definitions
  while (fgets(buf,sizeof(buf),fp)) {
    trimString(buf);
    // get code and procedure
    char *p = strtok(buf,",");
    int id = findCode(p);
    assert(id>=0); //Invalid procedure code in ordered procedures
    if( id >=0 ) orders->set(id);
  }
  fclose(fp);
  return orders;
}
void unbundlePanels(BitVector *procList)
{
  // this routine makes multiple passes through orders list in case
  // there is an occurance of a panel within a panel
  int changed;
  do{
    changed = FALSE;
    for(int i=procList->start();i<=procList->end() ;i++) {
      if( procList->get(i) &&
        procedures[i].isPanel) {
        procList->clear(i);
        procList->or(&procedures[i].panelProcs);
        changed = TRUE;
      }
    }
  } while(changed);
}
void dumpProcedureList(BitVector *procList)
{
  int numPanels = 0;
  int numProcs = 0;
  double totalFee = 0.0;
  // dump ordered procedures
  for(int i=procList- > start();i<=procList->end();i ++) {
    if( procList->get(i)) {
      numProcs++;
      totalFee += procedures[i].fee;
      if( procedures[i].isPanel) numPanels++;
      printf("%s - %s %s\n",
```

-continued

```
      procedures[i].code,procedures[i].desc, (char
*)((procedures[i].isPanel)?"(PANEL)":""));
    }
  }
  printf("\n");
  printf("Total panels: %d\n", numPanels);
  printf("Total procedures: %d\n", numProcs);
  printf("Total Fee for Listed Procedures: $%-5.2f\n", totalFee);
}
int panelProceduresMatch(Procedure *panelProc,BitVector *procList)
{
  // first check to see if panel proc is special chemistry procedure
    BitVector bv;
    bv.or(&panelProc->panelProcs);
    bv.and(procList);
    //printf("* * * *Dumping merged procedure list* * * *\n\n");
    //printf("Panel Procs\n");
    //dumpProcedureList(&panelProc->panelProcs);
    //printf("procList\n");
    //dumpProcedureList(procList);
    //printf("Merged\n");
    //dumpProcedureList(&bv);
    //printf("**** END OF DUMP ****\n\n");
    for(int i=bv.start();i<=bv.end();i++) {
      if( bv.get(i)) {
        printf(" Matched %s on procedure
%s\n",panelProc->code,procedures[i].code);
        return TRUE;
      }
    }
  return FALSE;
}
void dumpTree(TreeNode *node,int lvl)
{
TreeNode *pNode = (TreeNode *)node->branches.First();
int cnt = 0;
while(pNode) {
  printf("%*.*s%d:%d:",lvl,lvl,"
",lvl,cnt);
  for(int i=pNode->procedures.start();i<=pNode->procedures.end();i++) {
    if( pNode->procedures.get(i))
      printf("%s,",procedures[i].code);
    }
    printf("*\n");
    dumpTree(pNode,lvl+1);
    cnt ++;
    pNode = (TreeNode *)pNode->next;
  }
}
void buildTree(TreeNode *node,BitVector *procList)
{
TreeNode *pNode = new TreeNode;
assert(pNode);
pNode->procedures.or(procList);
node->branches.Insert(pNode);
for(int i=0;i<numProcedures;i++) {
  if( procedures[i].isPanel &&
    panelProceduresMatch(&procedures[i],procList)) {
// printf("Matched %s\n",procedures[i].desc);
    BitVector panelProcList(numProcedures,TRUE);
    panelProcList.clearAll();
    panelProcList.or(&procedures[i].panelProcs);
    panelProcList.and(procList);
    pNode = new TreeNode;
    assert(pNode);
    pNode->procedures.set(i); // set the panel ID
    node->branches.Insert(pNode);
    BitVector remainingProcList(numProcedures,TRUE);
    remainingProcList.or(procList);
    for(int j=panelProcList.start();j<=panelProcList.end();j++)
      if( panelProcList.get(j)) remainingProcList.clear(j);
    if( !remainingProcList.isNull())
      buildTree(pNode,&remainingProcList);
    }
  }
}
double calcFee(BitVector *procList)
{
  double totalFee = 0.0;
  // dump ordered procedures
  for(int i=procList->start();i<=procList->end();i++)
    if( procList->get(i))
      totalFee +=procedures[i].fee;
  return totalFee;
}
double getMinimumFee(TreeNode *node,BitVector *minProcs)
{
  TreeNode *pNode = (TreeNode *)node->branches.First();
  TreeNode *minNode = NULL;
  double fee = 0.0;
  BitVector minVector(numProcedures,TRUE);
  while(pNode) {
    double val = calcFee(&pNode->procedures);
    BitVector bv(numProcedures,TRUE);
    bv.clearAll();
    bv.or(&pNode->procedures);
    val = val + getMinimumFee(pNode,&bv);
    if( !minNode || val < fee) {
      minNode = pNode;
      fee = val;
      minVector.clearAll();
      minVector.or(&bv);
    }
    pNode = (TreeNode *)pNode->next;
  }
  minProcs->or(&minVector);
  return fee;
}
int main(int argc, char *argv[])
{
  printf("Dynamedix Medicare Billing Optimization Patent Algorithm\nUsing
  Dallas Locale and Carrier Code For Fee Structure");
  buildProcedureList("codes.txt");
  loadPanelDefinitions("panels.txt");
  //load the orders, build the tree and report the results
  BitVector *orders = loadOrders("orders.txt");
  // Unbundle and dump
  printf("\nOriginal Order\n\n");
  dumpProcedureList(orders);
  unbundlePanels(orders);
  printf("\nOriginal Order Unbundled with Duplicates Removed\n\n");
  dumpProcedureList(orders);
  printf("\n\nBuilding Tree Structure\n");
  TreeNode root;
  buildTree(&root,orders);
  dumpTree(&root,1);
  BitVector optOrder(numProcedures,TRUE);
  double fee = getMinimumFee(&root,&optOrder);
  printf("\n\nOptimum Order\n");
  dumpProcedureList(&optOrder);
  return 0;
}
```

What is claimed is:

1. A method of optimizing medical diagnosis, procedures and reimbursement claims using a structured search space, the method comprising:

listing a plurality of medical procedures to produce a master procedure list, wherein the master procedure list includes simple procedures and compound procedures which comprise at least two simple procedures;

associating a reimbursement to each of the plurality of medical procedures;

listing medical procedures for a specific medical encounter to produce a list of ordered procedures;

building a search tree of all possible combinations of the simple procedures and the compound procedures in the list of ordered procedures; and searching the search tree for the lowest total of values associated with the medical procedures in the list of ordered procedures, so as to determine a lowest reimbursement value combination.

2. The method of claim 1, wherein the master procedure list also includes a short description of the represented medical procedure; a long description of the represented medical procedure, and a list of all simple procedure that make up all compound procedures.

3. The method of claim 1, wherein the value associated with each of the plurality of medical procedures includes regional costs and fluctuations.

4. The method of claim 1, wherein building a search tree includes:
  matching compound procedures in the master procedure list to a plurality of simple procedures in the list of ordered procedure to produce a matched compound procedure;
  eliminating the plurality of simple procedures from the ordered procedure list; and
  adding the matched compound procedure to the ordered procedure list.

5. The method of claim 1, wherein the method further includes eliminating duplicates of simple procedures in the list of ordered procedures.

6. The method of claim 1, wherein the method is implemented on a palm sized computer.

7. The method of claim 1, wherein the method is implemented on a microprocessor based computer.

8. The method of claim 1, wherein the listing of the medical procedures is implemented by a medical professional at the medical encounter.

9. A computer program embodied on a computer system readable medium for optimizing medical diagnosis, procedures and reimbursement claims using a structured search space, the computer program comprising:
  instructions for listing a plurality of medical procedures to produce a master procedure list, wherein the master procedure list includes simple procedures and compound procedures which comprise of at least two simple procedures;
  instructions for associating a vale to each of the plurality of medical procedures;
  instructions for listing medical procedures for a specific medical encounter to produce a list of ordered procedures;
  instructions for building a search tree of all possible combinations of the simple procedures and the compound procedures in the list of ordered procedures; and
  instructions for searching tree for the lowest total of values associated with the medical procedures in the list of ordered procedures, so as to determine a lowest reimbursement value combination.

10. The computer program of claim 9, wherein the master procedure list also includes a short description of the represented medical procedure; a long description of the represented medical procedure, and a list of all simple procedure that make up all compound procedures.

11. The computer program of claim 9, wherein the value associated with each of the plurality of medical procedures includes regional costs and fluctuations.

12. The computer program of claim 9, wherein building a search tree includes:
  instructions for matching compound procedures in the master procedure list to a plurality of simple procedures in the list of ordered procedure to produce a matched compound procedure;
  instructions for eliminating the plurality of simple procedures from the ordered procedure list; and
  instructions for adding the matched compound procedure to the ordered procedure list.

13. The computer program of claim 12, wherein the computer program further includes instructions for eliminating duplicates of simple procedures in the list of ordered procedures.

14. The computer program of claim 9, wherein the computer program is implemented on a palm sized computer.

15. The computer program of claim 9, wherein the computer program is implemented on a microprocessor based computer.

16. The computer program of claim 9, wherein the instructions for listing of the medical procedures is implemented by a medical professional at the medical encounter.

17. A system for optimizing medical diagnosis, procedures and reimbursement claims using a structured search space, the system comprising:
  a master procedure list of plurality of medical procedures, wherein the master procedure list includes simple procedures and compound procedures which comprise at least two simple procedures;
  a reimbursement value associated with each of the plurality of medical procedures;
  a list of ordered procedures listing medical procedures for a specific medical encounter;
  a search tree of all possible combinations of the simple procedures and the compound procedures in the list of ordered procedures; and
  means for determining a minimum total combination of values associated with the medical procedures in the list of ordered procedures so as to determine a lowest reimbursement value combination.

18. The system of claim 17, wherein the master procedure list also includes a short description of the represented medical procedure; a long description of the represented medical procedure, and a list of all simple procedure that make up all compound procedures.

19. The system of claim 17, wherein the value associated with each of the plurality of medical procedures includes regional costs and fluctuations.

20. The system of claim 17, wherein the system is implemented on a palm sized computer.

21. The system of claim 17, wherein the system is implemented on a microprocessor based computer.

22. A system, comprising:
  a processor;
  a memory unit coupled to said processor, wherein said memory unit is operable for storing a computer program operable for optimizing medical diagnosis, procedures and claims, wherein the computer program includes instructions performing the following programming steps:
    listing a plurality of medical procedures to produce a master procedure list, wherein said master procedure list comprises simple procedures and compound procedures, wherein each of said compound procedures comprise at least two simple procedures;
    associating a reimbursement value to each of said plurality of medical procedures;
    listing medical procedures for a specific medical encounter to produce a list of ordered procedures;
    building a search tree of combinations of simple procedures and compound procedures in said list of ordered procedures.

23. The system as recited in claim 22, wherein said master procedure list comprises a description for each of said plurality of medical procedures and wherein said master procedure list includes a list of simple procedures that comprise compound procedures for each of said compound procedures in said master procedure list.

24. The system as recited in claim 22, wherein said value associated with each of said plurality of medical procedures comprises costs.

25. The system as recited in claim 22, wherein said programming step of building a search tree comprises the following programming steps:
   matching the components of said compound procedures in said master procedure list to a plurality of simple procedures in said list of ordered procedures to produce a matched compound procedure;
   eliminating said plurality of simple procedures in said list of ordered procedures; and adding said matched compound procedure to said list of ordered procedures.

26. The system as recited in claim 25, wherein the computer program is further operable for performing the following programming step:
   eliminating duplicates of simple procedures in said list of ordered procedures.

27. The system as recited in claim 22, wherein said search tree of combinations includes all possible combinations of compound procedures and simple procedures.

28. The system as recited in claim 22 further comprising:
   a touch-sensitive display device coupled to said processor, and wherein the computer program is further operable for performing the following programming step:
   searching said search tree for a lowest total of values associated with said medical procedures in said list of ordered procedures, so as to determine a lowest reimbursement value combination.

* * * * *